United States Patent [19]

Murai et al.

[11] 4,100,285
[45] Jul. 11, 1978

[54] N-SUBSTITUTED TRIALKOXYBENZYL PIPERAZINE DERIVATIVES

[75] Inventors: Hiromu Murai, Otsu; Yoshiaki Aoyagi, Kyoto, both of Japan

[73] Assignee: Nippon Shinyaku Co., Ltd., Kyoto, Japan

[21] Appl. No.: 783,561

[22] Filed: Apr. 1, 1977

[30] Foreign Application Priority Data

Apr. 9, 1976 [JP] Japan .................................. 51-40782
Apr. 9, 1976 [JP] Japan .................................. 51-40783
Apr. 9, 1976 [JP] Japan .................................. 51-40784

[51] Int. Cl.² .................. C07D 295/08; C07D 413/06
[52] U.S. Cl. .................................. 424/250; 544/121; 544/209; 544/357; 544/401; 544/398; 544/370; 542/470
[58] Field of Search ......... 260/268 R, 268 BC, 268 B; 424/250, 248.56; 544/121

[56] References Cited

U.S. PATENT DOCUMENTS 4,060,613  11/1977  Ferland et al. .................. 260/268 R Primary Examiner—Jose Tovar
Attorney, Agent, or Firm—Jacobs & Jacobs

[57] ABSTRACT

N-substituted trialkoxybenzyl piperazine derivatives expressed by the following general formula (I):

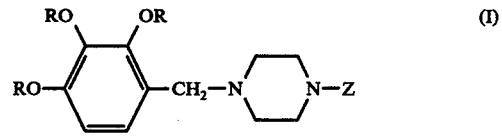

where R represents a methyl or ethyl group, and Z represents a group selected from the group consisting of the following groups: isopropenyl group, cinnamyl group, morpholino ethyl group, diaminotriazine group, hydantoinbutyl group,

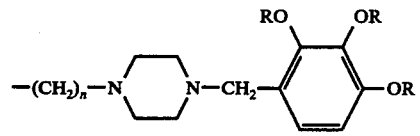

where R represents the same as above, and $n$ is an integer of 2 to 8, and

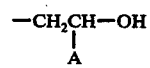

where A represents a group selected from the group consisting of hydrogen, lower alkyl group, hydroxymethyl group, phenyl group, naphthyloxymethyl group and

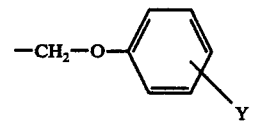

where Y represents a group selected from the group consisting of hydrogen, halogen, lower alkyl group, lower alkoxy group and hydroxy group.

15 Claims, No Drawings

N-SUBSTITUTED TRIALKOXYBENZYL PIPERAZINE DERIVATIVES

DETAILED DESCRIPTION OF THE INVENTION

This invention relates to N-substituted trialkoxybenzyl piperazine derivatives expressed by the following general formula (I):

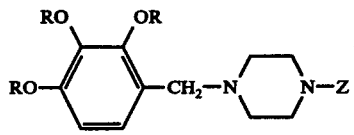

where R and Z represent the same as defined in the claim.

The compounds of this invention are novel materials which are not available in the literature and which have the excellent pharmacodynamic effects on the coronary circulation system such as coronary artery vasodilative action or cardiac movement controlling action and prove useful for medicinal preparations.

The cardiovascular activity of the compounds of this invention, as measured according to Langedorff's method by using the removed guinea pig heart, and $LD_{50}$ on mice are shown in Table 1 below. For administration of the compounds of this invention into the human body, it is recommended to give them at the dose of 10 to 500 mg/day for internal administration and 1 to 50 mg/day for intravenous aministration. The compounds can be administered as such or in combination with a pharmaceutical carrier conventionally employed in cardiovascular and like preparations.

Table 1

| | | Cardiovascular activity and $LD_{50}$ of the compounds of this invention | | | | |
|---|---|---|---|---|---|---|
| Example No. | Concentration (g/ml) | Coronary perfusion pressure (Δ%) | Heart Movements Amplitude | Tonus | Heart rate (Δ%) | $LD_{50}$ (mouse) mg/kg i.p. |
| 1 | $10^{-4}$ | 5.7 | ↓ | → | −18.2 | |
| 2 | $10^{-4}$ | −11.1 | ↓ | → | −60.3 | |
| 3 | $10^{-4}$ | 4.4 | ↓ | → | −21.9 | |
| 4 | $10^{-4}$ | −2.1 | ↑ | → | −8.6 | 567 |
| 5 | $10^{-4}$ | 3.8 | → | → | −9.3 | |
| 6 | $10^{-4}$ | −3.7 | ↓ | → | −11.7 | |
| 7 | $10^{-4}$ | −18.8 | ↓ | → | −37.5 | 239 |
| 8 | $10^{-4}$ | −19.2 | ↓ | → | −19.1 | 84 |
| 9 | $10^{-4}$ | −10.0 | ↓ | ↓ | −28.6 | |
| 10 | $10^{-4}$ | −4.4 | ↓ | ↓ | −10.7 | 567 |
| 11 | $10^{-4}$ | −11.1 | ↓ | → | −49.4 | 336 |
| 12 | $10^{-4}$ | −6.5 | ↓ | → | −16.1 | 724 |
| 13 | $10^{-4}$ | −16.0 | ↓ | → | −54.5 | 106 |
| 14 | $10^{-4}$ | −20.0 | ↓ | ↓ | −48.7 | 142 |

The compounds which are embraced within the scope of this invention can be synthesized by various methods, but the most general and simplest way is to react an alkyl halide or epoxy compound with a trialkoxybenzyl piperazine expressed by the following chemical structural formula (II) or (III):

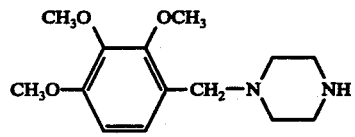

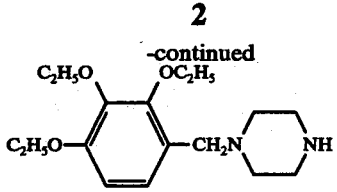

To synthesize a bis-compound, one mole of dihalogenoalkane is reacted with two moles of the material expressed by the above-shown structural formula (II) or (III).

The synthesis of the compounds of this invention may be also accomplished by the trialkoxybenzylation of alkylpiperazines or dipiperazinoalkanes or by the piperazine ring closure using an ethanolamine.

The present invention is described in further detail by way of some embodiments thereof, but it is to be understood that the scope of this invention is not limited to the compounds shown in these embodiments.

EXAMPLE 1 (R: methyl group (same in Examples 2 through 16); Z; Isopropenyl group)

5.0 gr of a hydrochloride of the material (II), 3.3 gr of isopropenyl bromide and 8.1 gr of potassium carbonate anhydride are dissolved in 150 ml of DMF and agitated at 50° C for 1 hour, and after cooling, the reaction product is refined by a silica gel column chromatograph and recrystallized from isopropanol as a hyrochloride. Melting point of the product: 205° – 210 ° C; yield: 2.5 gr. ($C_{19}H_{30}N_2O_3.2HCl$)

EXAMPLE 2 (Z: cinnamyl group)

5.0 gr of a hydrochloride of the material (II), 3.38 gr of cinnamyl chloride and 8.1 gr of potassium carbonate anhydride are mixed and agitated at 60° C for one hour, and after cooling, the reaction mixture is subjected to the same refining treatment as in Example 1 and then recrystallized from ethanol as a hydrochloride. Melting point (decomposed): 208° C; yield; 4.2 gr. ($C_{23}H_{30}N_2O_3.2HCl$)

EXAMPLE 3 (Z: diaminotriazine group)

5.0 gr of a hydrochloride of the material (II) is dissolved in 100 ml of ethanol in which 1.2 gr of metallic sodium has been dissolved, and this solution is further added with 4.0 gr of 2,4-diamino-6-chloro-S-triazine and 50 ml of dioxane and refluxed under agitation for 6 hours. The reaction product is evaporated to dryness under vacuum and the residual material is added with dilute caustic soda solution, and the precipitated crystals are filtered out and recrystallized from isopropanol, followed by additional recrystallization from dioxane as a hydrochloride. Melting point: 246° – 250° C; yield: 3.06 gr. ($C_{17}H_{25}N_7O_3 \cdot 2HCl$)

EXAMPLE 4 (Z: morpholinoethyl group)

10.4 gr of a hydrochloride of the material (II), 6.56 gr of morpholinoethyl chloride and 25.1 gr of potassium carbonate anhydride are dissolved in 150 ml of ethanol and refluxed under agitation for 4 hours, and after cooling, the mixture is subjected to a normal refining treatment and recrystallized from ethanol as a hydrochloride. Melting point (decomposed): 230° C; yield: 3.18 gr. ($C_{20}H_{33}N_3O_4 \cdot 3HCl \tfrac{1}{2} H_2O$)

EXAMPLE 5 (Z: hydantoinbutyl group)

6.8 gr of a hydrochloride of the material (II), 4.7 gr of bromobutylhydantoin and 5.0 gr of potassium carbonate anhydride are dissolved in 70 ml of DMF and agitated at 50° to 60° C for 2 hours, and the reaction mixture is subjected to a normal refining treatment and recrystallized from hydrous methanol as a hydrochloride. Melting point: 208° – 213° C: ($C_{21}H_{32}N_4O_5 \cdot 2 HCl \cdot H_2O$) yield: 4.0 gr.

EXAMPLE 6

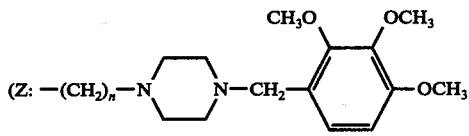

(same in Example 7 through 9). $n = 2$ 10.0 gr of a hydrochloride of the material (II), 13 gr of potassium carbonate anhydride and 5.6 gr of dibromoethane are dissolved in 100 ml of DMF and agitated under heating at 50° to 60° C for 3 hours. This mixture is then subjected to a proper treatment according to a normal method and the obtained basic material is recrystallized from acetone. Melting point: 121 – 122° C; yield: 3.9 gr. ($C_{30}H_{46}N_4O_6$)

EXAMPLE 7 ($n = 4$)

5.0 gr of a hydrochloride of the material (II), 9.0 gr of potassium carbonate anhydride and 1.0 gr of dichlorobutane are dissolved in 100 ml of DMSO and agitated under heating at 60° to 70° C for 10 hours, and the mixture is treated according to a normal method and the obtained basic material is extracted with chloroform. The chloroform extract is shaked with dilute hydrochloric acid and the hydrochloric acid layer is rendered alkaline, and the object material is extracted with ether. The extract is further added with 4 moles of maleic acid and recrystallized from isopropanol as a maleate. Melting point: 95° – 98° C; ($C_{32}H_{50}N_4O_6 \cdot 4C_4H_4O_4$) yield: 1.50 gr.

EXAMPLE 8 ($n = 6$)

6.7 gr of a hydrochloride of the material (II), 1.8 gr of dichlorohexane and 7.0 gr of potassium carbonate anhydride are dissolved in 70 ml of DMF and agitated under heating at 50° to 60° C for 16 hours, followed by a normal refining treatment, and the obtained basic material is extracted with chloroform, followed by back extraction with 1% acetic acid solution, and the object material is obtained from the acetic acid layer. It is further recrystallized from hydrous dioxane as a hydrochloride. Melting point (decomposed): 230° C; yield: 0.95 gr. ($C_{34}H_{54}N_4O_6 \cdot 4HCl$)

EXAMPLE 9 ($n = 8$)

9.0 gr of a hydrochloride of the material (II), 3.0 gr of dichlorooctane and 16 gr of potassium carbonate anhydride are dissolved in 70 ml of DMF and agitated under heating at 65° to 70° C for 12 hours, and the mixture is subjected to the same treatment as Example 8 and recrystallized from hydrous isopropanol as a hydrochloride. Melting point (decomposed): above 230° C; yield: 2.2 gr. ($C_{36}H_{58}N_4O_6 \cdot 4HCl$)

EXAMPLE 10-a (Z: -CH$_2$CH$_2$OH)

34 gr of a hydrochloride (melting point: 215° – 222° C) of the material (II) is dissolved under heating in 500 ml of ethanol having dissolved therein 5.0 gr of metallic sodium, and after cooling the mixture and filtering off the insolubles, ethanol is perfectly distilled off under vacuum. The residue is dissolved in 150 ml of DMF and added with 15 gr of β-bromohydrin and further with 15 gr of potassium carbonate anhydride, and the mixture is agitated under heating at 80 to 90° C for 3 hours. After cooling, it is diluted with water and extracted with ethyl acetate and the extract is recrystallized from ethanol as a hydrochloride. Melting point: 220° – 225° C; yield: 27.8 gr. ($C_{16}H_{26}N_2O_4 \cdot 2HCl$)

EXAMPLE 10-b (Z: -CH$_2$CH$_2$OH)

10 gr of a hydrochloride of the material (II) is added in 50 ml of ethanol containing 7.5 gr of triethylamine, and the mixture is refluxed under agitation for 30 minutes. After cooling the mixture, 34 ml of ethanol containing 2.0 gr of ethylene oxide is added dropwise under ice cooling and agitation for 10 minutes, followed by additional 3-hour agitation at room temperature. Ethanol is distilled off under vacuum, and the residue is treated in the same way as Example 10-a to obtain 8.8 gr of the object hydrochloride material.

EXAMPLE 10-c (Z: —CH$_2$CH$_2$OH)

45 gr of 2,3,4-trimethoxybenzaldehyde and 30 gr of N-β-hydroxyethylpiperazine are dissolved in 200 ml of ethanol and agitated under heating for 30 minutes, and the mixture, after cooling, is added with 5.0 gr of hydrogenated sodium borate under agitation and refluxed. This is followed by the same treatment as practiced in Example 10-a to obtain 41 gr of the object material (a hydrochloride).

EXAMPLE 10-d (Z: —CH$_2$CH$_2$OH)

19.6 gr of 2,3,4-trimethoxybenzaldehyde and 19.5 gr of N-β-hydroxyethylpiperazine are dissolved in 100 ml of ethanol, to which is further added 10 ml of formic acid under reflux, followed by additional 6-hour reflux. The reaction mixture is then subjected to the same treatment as in the preceding examples to obtain 17.0 gr of the object hydrochloride material.

EXAMPLE 10-e (Z: —CH$_2$CH$_2$OH)

4.33 gr of 2,3,4-trimethoxybenzyl chloride and 3.0 gr of N-β-hydroxyethylpiperazine are dissolved in 50 ml of ethanol, followed by addition of 2.0 gr of potassium carbonate and 6-hour agitation under reflux. The mixture is then subjected to the normal treatment to obtain 3.3 gr of the object material.

EXAMPLE 10-f (Z: —CH$_2$CH$_2$OH)

50 gr of N,N-bis-62 -chloroethyl-2,3,4-trimethoxybenzylamine hydrochloride (melting point: 127° - 131° C) and 50 gr of monoethanolamine are dissolved in 150 ml of ethanol and refluxed under heating for 30 minutes, followed by a usual refining treatment to obtain 32 gr of the object hydrochloride material.

EXAMPLE 11

1.33 gr of metallic sodium is dissolved in 100 ml of ethanol, which is further added with 10 gr of a hydrochloride of the material (II) and agitated for 30 minutes. Thereafter, 2.5 gr of propylene oxide is added dropwise for the period of 5 minutes, followed by 1-hour reflux under heating. The mixture is then treated by a usual method to obtain an oily reaction product and this product is treated with hydrochloric acid in ethanol and recrystallized from isopropanol as a hydrochloride. Melting point: 212° - 215° C; yield: 6.5 gr. (C$_{17}$H$_{28}$N$_2$O$_4$.2HCl$\frac{1}{2}$H$_2$O)

EXAMPLE 12

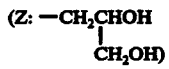

1.36 gr of metallic sodium is dissolved in 100 ml of ethanol, and this solution is further added with 10 gr of a hydrochloride of the material (II) and agitated for 30 minutes. Thereafter, 3.26 gr of glycidol is added dropwise for the period of 5 minutes, followed by 2-hour reflux under heating. The mixture is then treateed according to a usual method and the obtained basic material is extracted with n-butanol and the extract is treated with ethanol hydrochloric acid and recrystallized from ethanol as a hydrochloride. Melting point: 215° - 218° C; yield: 6.8 gr. (C$_{17}$H$_{28}$N$_2$O$_5$.2HCl)

EXAMPLE 13-a

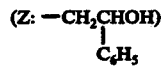

10 gr of a hydrochloride of the material (II) and 7.43 gr of triethylamine are refluxed in 50ml of ethanol under heating for 30 minutes, and after cooling, the mixture is further added with 5.25 gr of styrene oxide dropwise for the duration of 5 minutes and then refluxed under heating for 2 minutes. This is followed by an ordinary treatment and the obtained product is refined by a silica gel column chromatograph and recrystallized from isopropanol as a hydrochloride. Melting point: 170° 14 173° C; (C$_{22}$H$_{29}$N$_2$O$_5$.2HCl) yield: 3.5 gr. There is also obtained, as a side reaction product, a material of the general formula (I) where R is a methyl group and Z is -C$_6$H$_5$CHCH$_2$OH Melting point of this material (hydrochloride) is 177° - 182° C and yield is 0.7 gr.

EXAMPLE 13-b

0.14 gr of metallic sodium is dissolved in 10 ml of ethanol, which is further added with 2.0 gr of a hydrochloride of the material (II) and agitated for 30 minutes, followed by further addition of 12 gr of potassium carbonate and 1.7 gr of phenacyl bromide and 1-hour reflux under agitation. This mixture is then treated by a usual method to obtain 2.3 gr of an oily reaction product. Thus obtained 2.3 gr of N-phenacyl compound is dissolved in 20 ml of methanol, further added with 300 mg of hydrogenated sodium borate and refluxed. The refluxed material is then agitated at room temperature for 1 hour, further treated by a normal method and recrystallized from isopropanol as a hydrochloride. Melting point: 171° - 173° C; yield: 1.5 gr. (C$_{22}$H$_{29}$N$_2$O$_5$.2HCl)

EXAMPLE 14

6.0 gr of a hydrochloride of the material (II) is dissolved in 100 ml of ethanol, then added with 5.0 gr of triethylamine and agitated for 30 minutes. The mixture is further added with 3.75 gr of phenylglycidylether, refluxed under heating for 15 minutes, treated by a usual method and recrystallized from isopropanol as a hydrochloride. Melting point: 180° - 185° C; yield: 5.1 gr. (C$_{23}$H$_{32}$N$_2$O$_5$.2HCl.$\frac{1}{2}$H$_2$O)

EXAMPLE 15

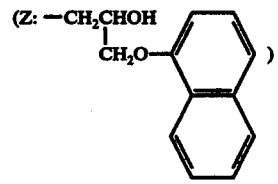

1.0 gr of the material (II) and 0.85 gr of α-naphthyl glycidyl are dissolved in 30 ml of dioxane and refluxed for 30 minutes. The reaction solution is distilled under vacuum and the residue is dissolved in isopropanol and HCl gas is passed there-through. The precipitated crystals are filtered off and recrystallized from isopropanol. Melting point (decomposed): 223° - 226° C; yield: 0.95 gr. (C$_{27}$H$_{36}$N$_2$O$_5$.2HCl)

EXAMPLE 16

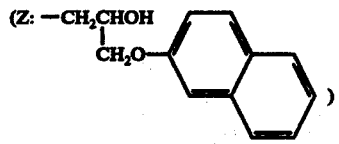

1.0 gr of the material (II) and 0.85 gr of β-naphthyl glycidyl ether are treated in the completely same way as Example 16 to obtain 0.97 gr of the object material.

Melting point (decomposed) : 214° – 217° C. (C₂₇H₃₆N₂O₅·2HCl)

(R: ethyl group (same in Examples 18 through 23)

EXAMPLE 17

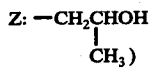
(Z: —CH₂CHOH
         |
         CH₃)

1.33 gr of metallic sodium is dissolved in 100 ml of ethanol, which is further added with 10 gr of a hydrochloride of the material (III) and agitated for 30 minutes. Thereafter, 2.5 gr of propylene oxide is added dropwise for the period of 5 minutes, followed by 1-hour reflux under heating. The mixture is then treated according to a usual method and the obtained oily material is treated with hydrochloric acid in ethanol and recrystallized from isopropanol as a hydrochloride. Melting point (decomposed): 214° – 218° C ; yield: 7.6 gr.(C₂₀H₃₄N₂O₄·2HCl

EXAMPLE 18

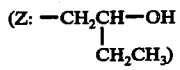
(Z: —CH₂CH—OH
         |
         CH₂CH₃)

1.33 gr of metallic sodium is dissolved in 100 ml of ethanol, followed by addition of 10 gr of a hydrochloride of the material (III) and 30-minute agitation for 30 minutes. Thereafter, 3.0 gr of butylene oxide is added dropwise for the period of 5 minutes and the mixture is refluxed under heating from 1 hour. This is followed by a proper treatment according to a usual method and the obtained reaction product is treated with hydrochloric acid in ethanol and recrystallized from isopropanol as a hydrochloride. Melting point : (decomposed): 212° – 215° C; yield: 6.9 gr. (C₂₁H₃₆N₂O₄·2HCl)

EXAMPLE 19

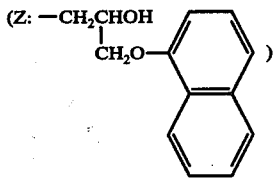
(Z: —CH₂CHOH
         |
         CH₂O—[naphthyl])

1.0 gr of the material (III) is dissolved in 30 ml of dioxane, followed by addition of 0.85 gr of α-naphthylglycidylether and 30-minute reflux under heating. The mixture is further treated according to a normal process and recrystallized from isopropanol as a hydrochloride. Melting point (decomposed): 212° – 217° C; (C₃₀H₄₀N₂O₅·2HCl) yield: 1.0 gr.

EXAMPLE 20

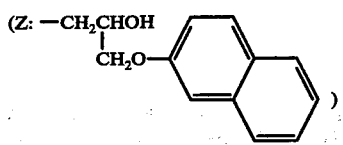
(Z: —CH₂CHOH
         |
         CH₂O—[naphthyl])

1.0 gr of the material (III) and 0.85 gr of naphthylglycidylether are treated in the completely same was as Example 19 to obtain 1.0 gr of the object material. Melting point (decomposed): 205° – 210° C. (C₃₀H₄₀N₂O₅·2HCl)

EXAMPLE 21

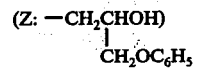
(Z: —CH₂CHOH)
         |
         CH₂OC₆H₅

1.0 gr of the material (III) is dissolved in 30 ml of methanol, and this is further added with 0.75 gr of phenylglycidylether, refluxed under heating for 45 minutes, treated according to a normal method and recrystallized from isopropanol as a hydrochloride. Melting point (decomposed): 209° – 213° C; yield: 1.48 gr. (C₂₆H₃₈N₂O₅·2HCl)

EXAMPLE 22

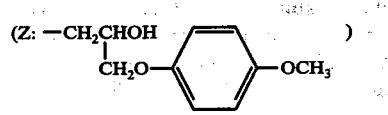
(Z: —CH₂CHOH
         |
         CH₂O—[C₆H₃]—OCH₃)

A mixture of 2.2 gr of N-3-(4-methoxy)-2-hydroxypropylpiperazine dihydrochloride (m.p. 190°–194° C) and 2.0 gr of 2,3,4-triethoxybenzaldehyde is dissolved in 100 ml of formic acid and the mixture is refluxed at 70–80° C for 24 hours. The reaction solution is evaporated in vacuo, the residue is diluted with water, washed with benzene, made alkaline with sodium hydroxide, and extracted with benzene. The extract is purified by a silica gel column chromatography, converted to a hydrochloride, and recrystallized from ethanol. C₂₇H₄₀N₂O₆·2HCl. Melting point: 199°–204° C (decompn). Yield: 0.61 gr.

EXAMPLE 23

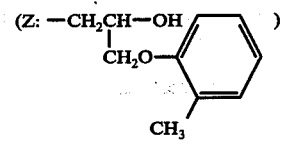
(Z: —CH₂CH—OH
         |
         CH₂O—[C₆H₃]
         CH₃)

A mixture of 1.72 gr of 2,3,4-triethoxybenzyl chloride and 1.60 gr of N-3-(2-methylphenoxy)-2-hydroxypropylpiperazine dihydrochloride (m.p. 157°–161° C) is added to 50 ml of DMF and the mixture is heated with 5.0gr of anhydrous potassium carbonate at 60°–70° C for 4 hr with agitation. The reaction mixture is then diluted with dil. hydrochloric acid, washed with benzene, made alkaline with sodium hydroxide, and extracted with benzene. The extract is converted to a hydrochloride and recrystallized from isopropanol. C₂₇H₄₀N₂O₅·2HCl. Melting point: 209°–212° C (decompn). Yield: 1.67 gr.

EXAMPLES 24 TO 40

More 17 compounds are similarly prepared by the process disclosed in the Example 14. They are listed in the following Table 2.

Table 2

Z: —CH$_2$CHOH
       |
      CH$_2$O—Y

| Example No. | R: | A: | molecular formula | M P |
|---|---|---|---|---|
| 24 | —CH$_3$ | 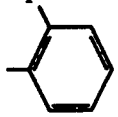 2-F-C$_6$H$_4$— | C$_{23}$H$_{31}$N$_2$O$_5$F · 2HCl | 200–203° C(decomp.) |
| 25 | " |  4-F-C$_6$H$_4$— | C$_{23}$H$_{31}$N$_2$O$_5$F · 2HCl | 208–209° C(decomp.) |
| 26 | " | 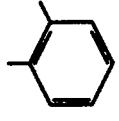 2-Cl-C$_6$H$_4$— | C$_{23}$H$_{31}$N$_2$O$_5$Cl · 2HCl | 205–206° C(decomp.) |
| 27 | " |  4-Cl-C$_6$H$_4$— | C$_{23}$H$_{31}$N$_2$O$_5$Cl · 2HCl | 207–208° C(decomp.) |
| 28 | " |  4-Br-C$_6$H$_4$— | C$_{23}$H$_{31}$N$_2$O$_5$Br · 2HCl | 219–221° C(decomp.) |
| 29 | " | 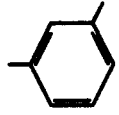 2-CH$_3$-C$_6$H$_4$— | C$_{24}$H$_{34}$N$_2$O$_5$ · 2HCl | 206–208° C(decomp.) |
| 30 | " |  4-CH$_3$-C$_6$H$_4$— | C$_{24}$H$_{34}$N$_2$O$_5$ · 2HCl | 190–196° C(decomp.) |
| 31 | " |  4-C$_2$H$_5$-C$_6$H$_4$— | C$_{25}$H$_{36}$N$_2$O$_5$ · 2HCl · H$_2$O | 205–207° C(decomp.) |
| 32 | " | 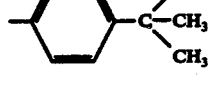 4-C(CH$_3$)$_3$-C$_6$H$_4$— | C$_{27}$H$_{40}$N$_2$O$_5$ · 2HCl | 218–222° C(decomp.) |
| 33 | " | 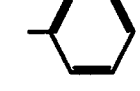 2-CH$_3$O-C$_6$H$_4$— | C$_{24}$H$_{34}$N$_2$O$_6$ · 2HCl | 200–202° C(decomp.) |
| 34 | " | 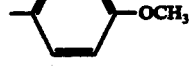 4-CH$_3$O-C$_6$H$_4$— | C$_{24}$H$_{34}$N$_2$O$_6$ 2HCl | 202–205° C(decomp.) |
| 35 | " | 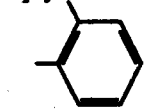 2-C$_2$H$_5$O-C$_6$H$_4$— | C$_{25}$H$_{36}$N$_2$O$_6$ · 2HCl½H$_2$O | 201–205° C(decomp.) |

Table 2-continued

Z: $-CH_2CHOH$
         $|$
        $CH_2O-Y$

| Example No. | R: | A: | molecular formula | M P |
|---|---|---|---|---|
| 36 | " | 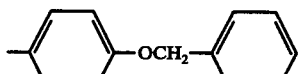 | $C_{30}H_{38}N_2O_6 \cdot 2HCl$ | 200-202° C(decomp.) |
| 37 | " | 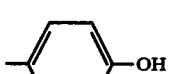 | $C_{23}H_{32}N_2O_6 2HCl$ | 220-223° C(decomp.) |
| 38 | $-C_2H_5$ |  | $C_{26}H_{37}N_2O_5F \cdot 2HCl$ | 225-229° C(decomp.) |
| 39 | " | 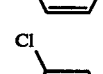 | $C_{26}H_{37}N_2O_5Cl \cdot 2HCl$ | 210-214° C(decomp.) |
| 40 | " | 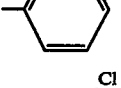 | $C_{26}H_{37}N_2O_5Cl \cdot 2HCl$ | 212-218° C(decomp.) |

What is claimed is:

1. A compound of the formula:

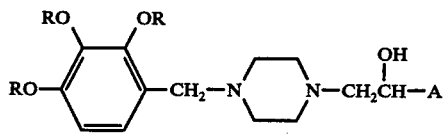

wherein each

R independently of the other is methyl or ethyl; and
A is hydrogen, methyl, ethyl, hydroxymethyl, phenyl, naphthyloxymethyl or phenoxymethyl unsubstituted or substituted by chloro, bromo, fluoro, hydroxy, methoxy, ethoxy, benzyloxy or alkyl of 1 to 4 carbon atoms, and the pharmaceutically acceptable acid addition salts thereof.

2. A compound according to claim 1 wherein each R is methyl.

3. A compound according to claim 1 wherein A is hydrogen, hydroxymethyl or phenoxymethyl unsubstituted or substituted by chloro, hydroxy or methoxy.

4. The hydrochloride salt of a compound according to claim 1.

5. The compound according to claim 1 wherein each of R is methyl and A is hydrogen, hydroxymethyl or phenoxymethyl unsubstituted or substituted by chloro, hydroxy or methoxy.

6. The compound according to claim 1 which is N-(2,3,4-trimethoxybenzyl)-N'-(2-hydroxyethyl)piperazine, or the hydrochloride salt thereof.

7. The compound according to claim 1 which is N-(2,3,4-trimethoxybenzyl)-N'-(2,3-dihydroxypropyl)piperazine, or the hydrochloride salt thereof.

8. The compound according to claim 1 which is N-(2,3,4-trimethoxybenzyl)-N'-(2-hydroxy-3-phenoxypropyl)piperazine, or the hydrochloride salt thereof.

9. The compound according to claim 1 which is N-(2,3,4-trimethoxybenzyl)-N'-[2-hydroxy-3-(4-chlorophenoxy)-propyl]piperazine, or the hydrochloride salt thereof.

10. The compound according to claim 1 which is N-(2,3,4-trimethoxybenzyl)-N'-[2-hydroxy-3-(4-methoxyphenoxy)-propyl]piperazine, or the hydrochloride salt thereof.

11. The compound according to claim 1 which is N-(2,3,4-trimethoxybenzyl)-N'-[2-hydroxy-3-(4-hydroxyphenoxy)-propyl]piperazine, or the hydrochloride salt thereof.

12. A pharmaceutical composition useful for improving the cardiovascular activity of a human or animal, which comprises a therapeutically effective amount of the compound of claim 1 in combination with a pharmaceutical carrier.

13. A method for improving the cardiovascular activity of a human or animal, which comprises administering to a human or animal in need thereof a therapeutically effective amount of the compound of claim 1.

14. The compound N-(2,3,4-trimethoxybenzyl)-N'-(2-morpholinoethyl)piperazine, or the trihydrochloride salt thereof.

15. A compound of the formula:

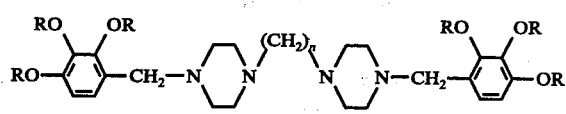

wherein each

R is independently methyl or ethyl; and n has a value of from 2 to 8, and the pharmacetically acceptable acid addition salts thereof.

* * * * *